United States Patent
Filipi

(10) Patent No.: US 8,973,573 B2
(45) Date of Patent: Mar. 10, 2015

(54) BITE BLOCK WITH AIRWAY MOUNT

(75) Inventor: Charles J. Filipi, Omaha, NE (US)

(73) Assignee: Creighton University, Omaha, NE (US)

( * ) Notice: Subject to any disclaimer, the term of this patent is extended or adjusted under 35 U.S.C. 154(b) by 276 days.

(21) Appl. No.: 12/825,918

(22) Filed: Jun. 29, 2010

(65) Prior Publication Data

US 2010/0326435 A1    Dec. 30, 2010

Related U.S. Application Data

(60) Provisional application No. 61/221,545, filed on Jun. 29, 2009.

(51) Int. Cl.
*A61M 16/00* (2006.01)
*A62B 9/06* (2006.01)
*A61M 16/04* (2006.01)

(52) U.S. Cl.
CPC ....... *A61M 16/0488* (2013.01); *A61M 16/0497* (2013.01); *A61M 16/0493* (2014.02)
USPC ................. 128/200.26; 128/207.14

(58) Field of Classification Search
USPC .......... 128/200.24, 200.26, 207.14, 861, 859, 128/912
See application file for complete search history.

(56) References Cited

U.S. PATENT DOCUMENTS

| | | | |
|---|---|---|---|
| 2,908,269 A | 3/1958 | Cheng | |
| 3,756,244 A | 9/1973 | Kinnear | |
| 3,774,616 A | 11/1973 | White et al. | |
| 4,166,467 A | 9/1979 | Abramson | |
| 4,214,594 A * | 7/1980 | Little | 607/122 |
| 4,235,229 A * | 11/1980 | Ranford et al. | 128/207.17 |
| 4,270,529 A | 6/1981 | Muto | |
| 4,270,531 A | 6/1981 | Blachly | |
| 4,351,331 A | 9/1982 | Gereg | |
| 4,425,911 A | 1/1984 | Luomanen et al. | |
| D283,158 S | 3/1986 | Jackson | |
| 5,009,227 A | 4/1991 | Nieuwstad | |
| 5,174,284 A | 12/1992 | Jackson | |
| 5,390,661 A | 2/1995 | Griffith et al. | |
| 5,413,095 A * | 5/1995 | Weaver | 128/200.26 |
| 5,421,327 A | 6/1995 | Flynn et al. | |
| 5,443,063 A | 8/1995 | Greenberg | |
| 5,513,643 A | 5/1996 | Jackson | |
| 5,590,643 A | 1/1997 | Flam | |
| 5,620,408 A | 4/1997 | Vennes et al. | |

(Continued)

FOREIGN PATENT DOCUMENTS

| | | | |
|---|---|---|---|
| IL | WO2009/066277 | * | 5/2009 |
| KR | 200395743 | | 9/2005 |

(Continued)

OTHER PUBLICATIONS

Search Report for WO2008/144768; PCT/US2008/064438.

(Continued)

*Primary Examiner* — Justine Yu
*Assistant Examiner* — Michael Tsai
(74) *Attorney, Agent, or Firm* — Woodard, Emhardt, Moriarty, McNett & Henry LLP

(57) ABSTRACT

A bite block 20 for use during transoral medical procedures has a main lumen 42 and a side mount 110 for receiving a separately inserted airway 160. The airway 110 may be a commercially available nasopharangeal airway which is inserted in mount 110 and extends into the oral cavity so as to effectively function as oral pharangeal airway.

7 Claims, 4 Drawing Sheets

(56) References Cited

U.S. PATENT DOCUMENTS

| | | |
|---|---|---|
| 5,653,229 A | 8/1997 | Greenberg |
| 5,746,202 A * | 5/1998 | Pagan ................... 128/207.14 |
| 6,244,865 B1 | 6/2001 | Nelson et al. |
| 6,257,238 B1 | 7/2001 | Meah |
| 6,361,540 B1 | 3/2002 | Gauderer et al. |
| 6,474,332 B2 | 11/2002 | Arndt |
| 6,517,549 B1 | 2/2003 | Dennis |
| 6,743,017 B2 | 6/2004 | O'Neill |
| 6,983,744 B2 | 1/2006 | Alfery |
| 7,077,841 B2 | 7/2006 | Gaiser et al. |
| 7,100,612 B2 * | 9/2006 | Dunlap ................... 128/207.18 |
| 7,160,270 B2 | 1/2007 | West et al. |
| 7,171,962 B1 * | 2/2007 | Bloem ................... 128/200.26 |
| 7,624,736 B2 * | 12/2009 | Borody ................... 128/848 |
| 7,766,008 B2 * | 8/2010 | Manishen ................ 128/200.26 |
| 7,934,505 B2 * | 5/2011 | Garren et al. ................. 128/859 |
| 2002/0099387 A1 | 7/2002 | Gauderer et al. |
| 2002/0151871 A1 | 10/2002 | Gaiser et al. |
| 2003/0217744 A1 | 11/2003 | Sugai et al. |
| 2006/0149185 A1 | 7/2006 | Gaiser et al. |
| 2006/0272647 A1 | 12/2006 | Hauge |
| 2007/0006878 A1 | 1/2007 | Mackey et al. |
| 2007/0113844 A1 * | 5/2007 | Garren et al. ............ 128/200.26 |
| 2007/0129735 A1 | 6/2007 | Filipi |
| 2008/0210232 A1 * | 9/2008 | Trodler ................... 128/200.26 |
| 2008/0275473 A1 | 11/2008 | Filipi |

FOREIGN PATENT DOCUMENTS

| | | |
|---|---|---|
| WO | WO 2007/067919 A2 | 6/2007 |
| WO | WO 2007/067919 A3 | 6/2007 |
| WO | WO 2008/144768 | 11/2008 |

OTHER PUBLICATIONS

U.S. Appl. No. 12/623,882 to Filipi, Office Action mailed Jun. 21, 2013.

* cited by examiner

BITE BLOCK WITH AIRWAY MOUNT

RELATED APPLICATION DATA

This application claims the benefit of U.S. Provisional App. Ser. No. 61/221,545, filed Jun. 29, 2009, which is hereby incorporated by reference.

TECHNICAL FIELD

The present invention is generally related to bite blocks for use during surgical procedures. More particularly, but not exclusively, it relates to novel bite blocks for use during transoral procedures.

BACKGROUND

Bite blocks are used in a variety of transoral procedures and generally serve to hold the patient's mouth open and provide an access path for surgical instruments. However, many commercially available bite blocks suffer from a number of defects, such as being are too easily dislodged, being uncomfortable, or failing to provide adequate working area for the instruments which are introduced during the transoral procedure. Furthermore, during some transoral procedures the operating physician may find it desirable to take steps to positively maintain an airway without unduly restricting the ability to operate the instruments.

Accordingly, there are needs for improvements in the art. In one form the present application provides improved bite block designs and methods of construction that address one or more of the needs outlined above.

SUMMARY

Figure 1:
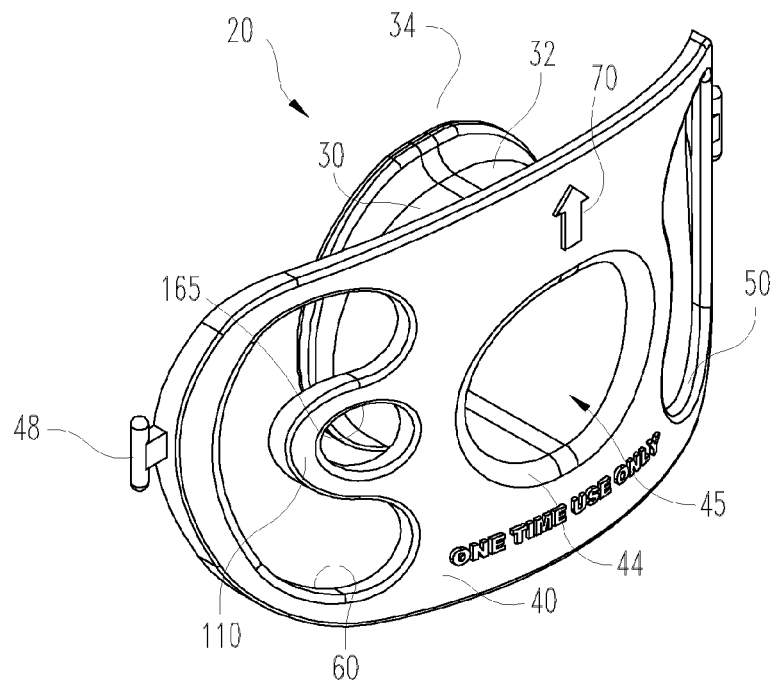
FIG. 1 is a perspective view of a bite block with an airway mount according to one embodiment of the present invention.

The present invention provides novel bite blocks for use in performing transoral procedures. While the actual nature of the invention covered herein can only be determined with reference to the claims appended hereto, certain aspects of the invention that are characteristic of the embodiments disclosed herein are described briefly as follows.

In one form, what is provided is the combination of a bite block and a nasopharyngeal airway (NPA) wherein, rather than being inserted nasally, the NPA is mounted to the bite block and extends into the oral cavity so as to effectively function as an oral pharyngeal airway. The bite block may include a main bite block body defining an operating lumen and an airway mount configured such that the airway is outside the main operating lumen. The bite block may include an outer face defining a pair of side openings on either side of a main instrument lumen and the airway mount for the NPA may be provided in one of the side openings of the outer face. The airway mount may be molded integrally with the bite block and positioned such that the NPA is generally aligned with the centerline of the main instrument lumen.

In another from, what is provided is a bite block having a main instrument lumen and a relatively small diameter airway mount wherein the airway mount is configured to hold a relatively small diameter piece of flexible tubing which would extend into the oral cavity past the distal end of the main instrument lumen, wherein the airway mount has an effective inner diameter which is between 25% and 50% of the effective inner diameter of the main instrument lumen. The bite block may include an outer face adapted to be positioned outside the patient's mouth during use and defining a pair of side openings wherein one of the side openings is provided with the airway mount. The mount may be configured to hold a nasopharyngeal airway such that it extends into the oral cavity and functions as an oral pharyngeal airway.

In another form, what is provided is a bite block for use with a nasopharyngeal airway. The bite block comprises a main bite block body defining upper and lower outer surfaces adapted to be positioned between a patient's upper and lower teeth respectively and defining an operating lumen for providing instrument access. The bite block also includes an outer face adapted to be positioned outside the patient's mouth during use. The outer face defines a pair of side openings, and a mount is configured so as to hold a nasopharyngeal airway in one of the side openings such that the nasopharyngeal airway functions as an oral pharyngeal airway. The mount may be molded integrally with the bite block. The mount may be disposed within one of the side openings such that it contacts the interior surface of the side opening in at least two separate locations. The mount may be asymmetrical with respect to the longitudinal axis of the bite block. The mount may be configured to mate with the flared end of the nasopharyngeal airway in a friction fit or snap fit arrangement. The mount may define opposing interior surfaces which are curved and tapered in correspondence with the curvature and taper of the proximal end portion of the nasopharyngeal airway.

These and other aspects are described more fully below.

DESCRIPTION

Referring now to FIGS. 1-5, a bite block 20 includes a main bite bock body 30 adapted to be positioned in a patient's mouth such that the upper and lower surfaces 32, 36 are facing the upper and lower teeth (not shown) respectively. Bite block 20 includes a front face 40 which is adapted to be outside the patient and upper and lower flanges 34, 38, which are adapted to be inside the patient's mouth just behind the upper and lower teeth (not shown). The side ends of the face 40 are provided with a pair of fasteners 48 for connection to a head strap (not shown) which would wrap about the patient's head and serve to secure the bite block in position. The fasteners 48 are illustrated as conventional T-shaped fasteners that may be coupled to a conventional elastic head strap.

Front face 40 of bite block 20 also defines a pair of side or wing openings 50, 60, on the right and left sides of instrument lumen 42 respectively, wherein the front fact includes an arrow 70 which, when in use, would be pointing toward the patient's forehead. These side openings 50, 60 may be used to provide additional access to the oral cavity during a procedure, for example for purposes of providing suction. To facilitate this use, one or both of the side openings 50, 60 may be sized and configured to allow passage of rigid tubes having an outer diameter up to at least about 14 mm.

Front face 40 of bite block 20 also defines a pair of side or wing openings 50, 60, on the right and left sides of instrument lumen 42 respectively, wherein the front fact includes an arrow 48 which, when in use, would be pointing toward the patient's forehead. These side openings 50, 60 may be used to provide additional access to the oral cavity during a procedure, for example for purposes of providing suction. To facilitate this use, one or both of the side openings 50, 60 may be sized and configured to allow passage of rigid tubes having an outer diameter up to at least about 14 mm.

An airway mount 110 is disposed in the left side opening 60, and the purpose of the airway mount 110 is to secure an airway to the bite block 20 such that the airway extends from the side opening 60 distally into the oral cavity and substantially past the distal end of the main lumen 42 so as to effectively provide a positive airway during a procedure. The airway mount 110 may be designed to accommodate any flexible tube having sufficient diameter, length, and rigidity to positively maintain an airway.

In a preferred form, the airway mount 110 is specifically designed to accommodate a nasopharyngeal (NPA), which are commercially available airways designed to be used nasally. Nasopharyngeal airways 160, which are sometime referred to as nasal trumpets, have the shape of an elongated flexible tube with a flared, or trumpet, end 162. In the conventional use of an NPA, the elongated tube is inserted into a patient's nasal passage with the flared end 162 abutting against the nostril and serving to prevent the NPA from going into the nasal cavity. Surprisingly, applicants have found that NPAs work well when inserted into the oral cavity so as to function as an oral pharyngeal airway.

In the illustrated embodiment, airway mount 110 is in the form of a ring defining a relatively small diameter mounting hole 165 that is generally aligned with the horizontal centerline of the bite block main lumen 42. The internal surfaces of the mounting hole 165 are oriented so as to define a longitudinal mounting axis generally parallel to the longitudinal axis defined by the main lumen 42, and the inner diameter of the hole 165 is chosen to accommodate the elongated tube section of a standard NPA 160 but not the flared end 162. In one form, the effective inner diameter of mounting hole 165 is in between about 7-12 mm or about 9. In other forms, the effective inner diameter of hole 165 is between about 25% and 50% of the effective inner diameter of the main lumen 42. In other forms, the inner diameter of mounting hole 165 in the range of 9-15 mm, 5-12 mm, 5-15 mm, 6-14 mm, 7-13 mm, 8-12 mm or 8-11 mm.

Figure 5:
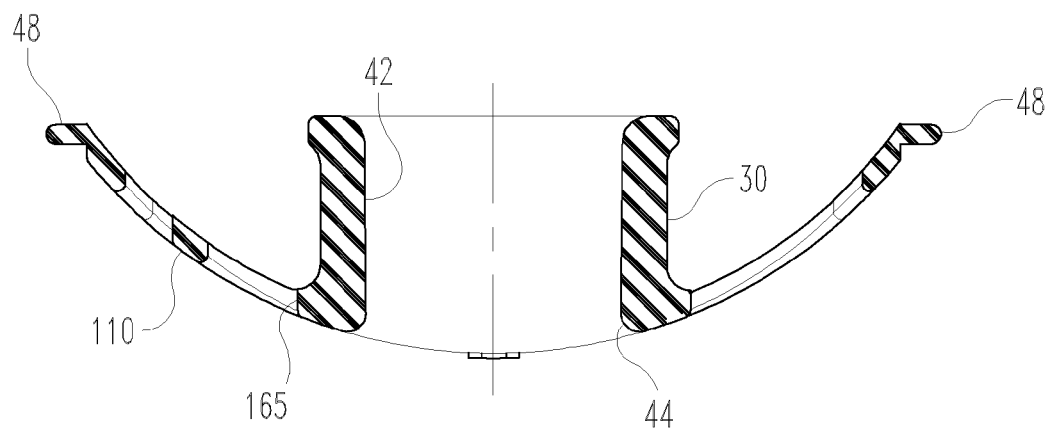
FIG. 5 is a top cross sectional view of the FIG. 1 bite block.
Figure 6:
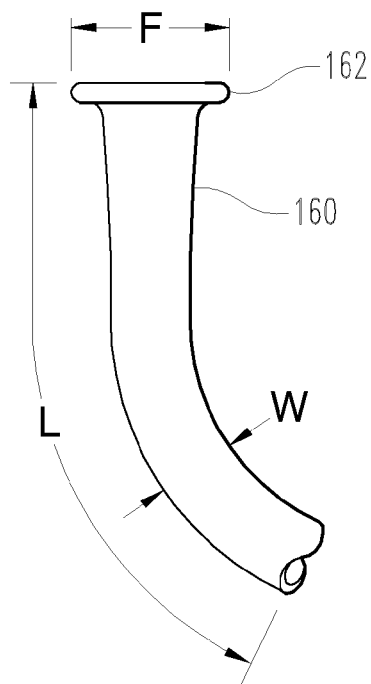
FIG. 6 is a perspective view of a nasopharyngeal airway.
Figure 7:
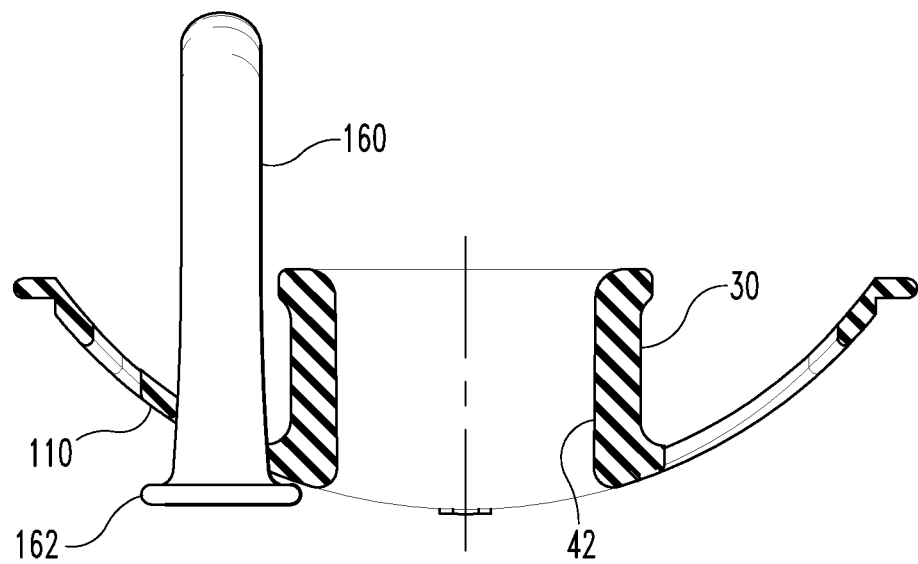
FIG. 7 shows a top view of the FIG. 6 airway inserted into the mounting hole of the FIG. 1 bite block, wherein the bite block is shown in cross section as per FIG. 5.

When inserted as shown in FIG. 7, the airway 160 is maintained in position via a friction fit. The upper and lower sections 110a, 110b of the mounting ring extend from interior surfaces of the left side opening 60 near the main body 30 and are curved distally to match the overall curvature of the outer face, as shown in FIG. 5. Accordingly, the ring is in the form of an oval which encircles the airway 160 at an acute angle to the longitudinal axis of the airway 160 such that different portions of the mounting ring contact the outer surface of the airway in different longitudinal positions. In other words, the mounting hole 165 is asymmetric relative to the longitudinal axis of the airway 160 with the right side of the mounting hole 165 near the main lumen (at 165 in FIG. 5) contacting a portion of the airway 160 which is proximal to the portion contacted by the left side of the mounting hole 165 opposite the main lumen 30. The asymmetry helps to maintain the airway 160 in position and to provide increased frictional resistance to the airway being accidentally expelled by the patient's tongue. Alternatively, the airway mount 110 may be symmetrical with respect to the longitudinal axis of the airway 160.

Figure 8:
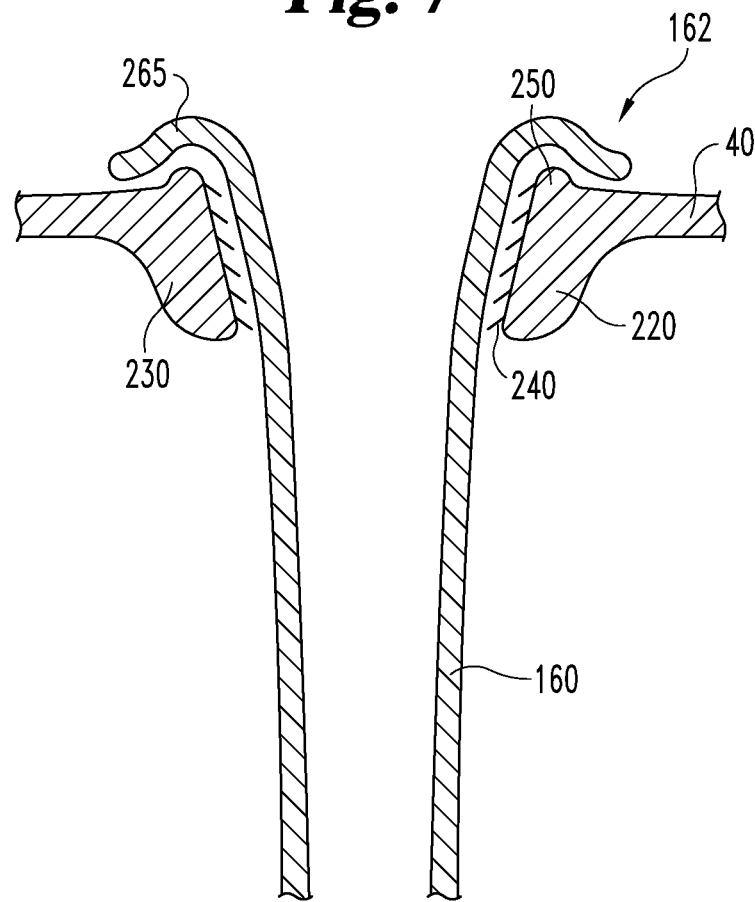
FIG. 8 shows an enlarged cross sectional view of an airway in a mounting hole of a bite block according to another embodiment.

Optionally, airway mount 110 may also be configured with means to enhance the friction fit with a standard NPA so as to reduce the chance that the NPA would be extruded by the patient. With reference to FIG. 8, the airway mount may include oppositely disposed mounting members 220, 230 which provide an engagement surface for the trumpet end of the NPA. The engagement surface may be inwardly tapered so as to match the outer taper of the trumpet end of the NPA. As illustrated, the mounting members 220, 230 have a thickness greater than the thickness of the adjacent face plate 40 so as to increase the surface area provided for engagement with the body of the airway 160. The tapered engagement surface may optionally be provided with gripping teeth 240 or a rubberized surface to further enhance the friction fit. As shown, the mounting members also include rounded shoulders 250 which extend above the adjacent surface of the face plate 40. These shoulders 250 are designed to mate with the underside of the flared end 162 of the NPA in a press fit engagement.

The airway mount 110 may be located in other locations within the left side hole 60, such as in the upper or lower lobes of the side hole 60, or in the right side hole 50. Alternatively, airway mount 110 may be aligned with one of the side openings 50, 60 but coupled to a different portion of the bite block 20, such the main body 30 or some other portion of the front face 40. The airway mount 110 can be provided as an attachment to the bite block, but preferably the mount 110 is molded integrally with the bite block. Alternatively or in addition, a strap may be used to secure the NPA to the biteblock.

Bite block 20 may be formed from any number of biocompatible or food grade synthetic or polymeric materials. The material may be selected such that bite block 20 may be formed by a conventional molding process, such as injection molding. Preferably, the material is selected to be relatively resilient plastic.

In one form, the bite block material has a Shore D Durometer hardness (calculated per ASTM D2240) less than 65, more typically in the range about 45 to about 60. In another form, the bite block material is a low density polymer mixture, for example having a density below 9.4 g/cm$^3$. One suitable material is Paxothene NA207-66 available from USI Corporation (Taipei, Taiwan), which is a low density polyethylene (LDPE) having a density of 0.921 g/cm$^3$ and a Shore D hardness of 53.

Figure 3:
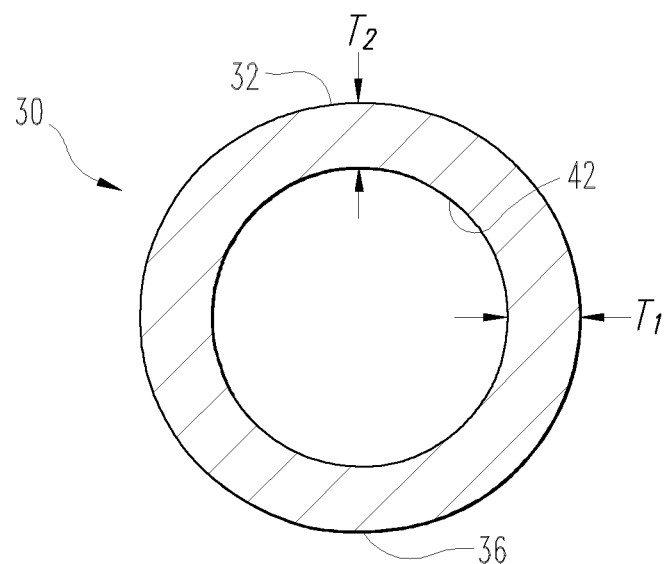
FIG. 3 shows the cross sectional profile as indicated in FIG. 2.
Figure 4:
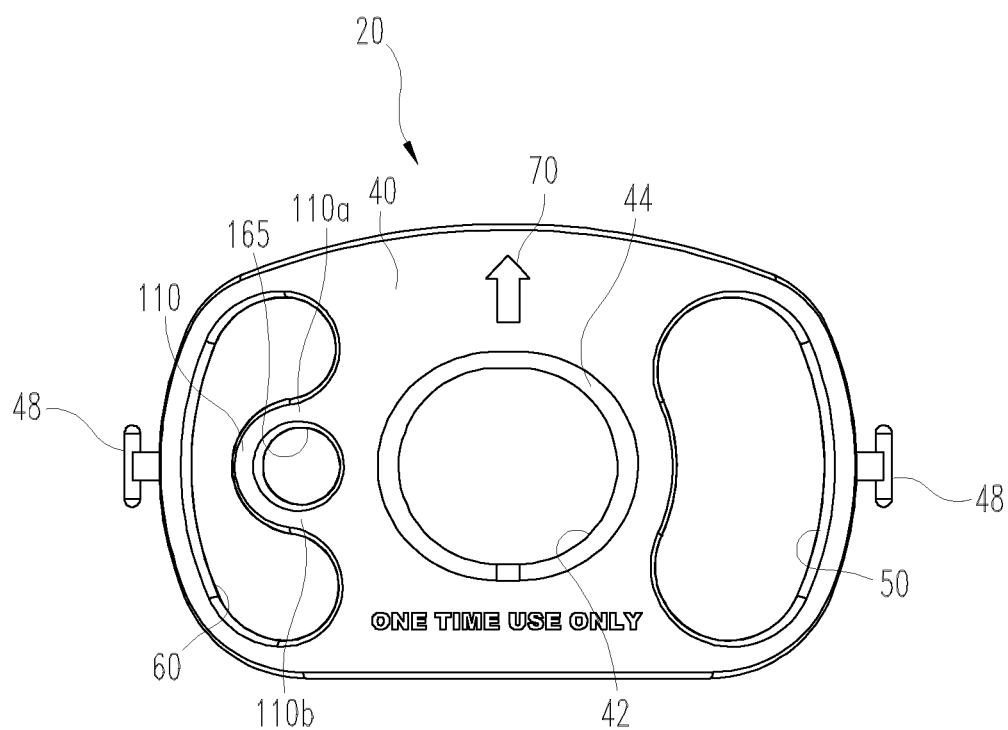
FIG. 4 is a front elevational view of the FIG. 1 bite block.

Referring to the cross sectional schematic depicted in FIG. 3, the side wall thickness $T_1$ and the upper and lower wall thickness $T_2$ of the main body 30 are preferably chosen such that the resulting structure resists compression under an applied bite load up to about 33 lbs. Such a compressive force may cause slight deformation to the inner dimensions, but preferably, block body 30 is designed such that the effective inner diameter of instrument lumen 42 is at least 20 mm under a bite load of about 30 lbs. For example $T_1$ and $T_2$ may be in the range of about 3-7 mm, for example, between 4-6 mm. In one implementation, $T_1$ is about 5.7 mm and $T_2$ is about 5.0 mm. In comparison, for conventional bite blocks constructed from high density polyethylene (HDPE), which would typically have a Shore D hardness above 65, a typical wall thickness may be only about 2 mm.

Figure 2:
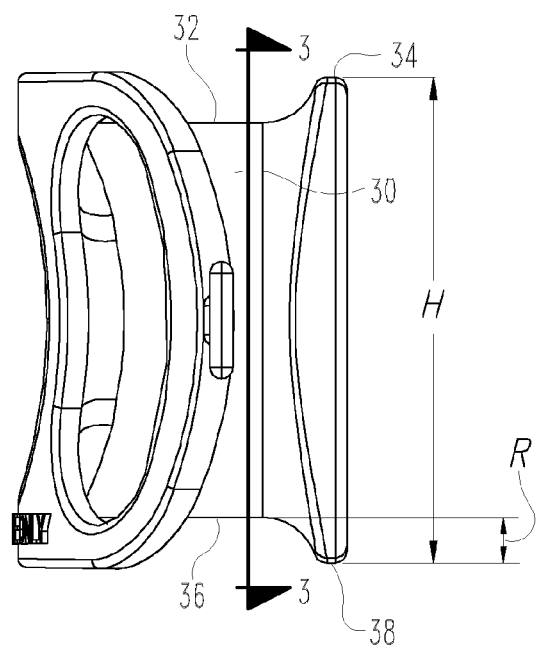
FIG. 2 is a right side elevational view of the FIG. 1 bite block.

Upper and lower lip portions 34, 38 rise above the upper and lower surface portions 32, 36 to form a retaining flange or lip. With reference to FIG. 2, the rise R from the tooth landing to the top of a respective retaining lip is preferably in the range of 3-5 mm, for example, about 3.5 mm. The overall height H between the upper and the lower retaining flanges is preferably in the range of about 35 mm to about 45 mm, for example between 40 and 45 mm, for example about 41 mm. By comparison, known commercially available bite blocks have a slightly lower lip rise (R) and an overall retaining flange height (H) of around 31.5 mm. The larger overall height H makes it harder for the patient to expel the block, because the patient would need to open his mouth wider to clear the flange.

Nasopharyngeal airways (NPAs) which may be used are commercially available from a number of manufacturers. One example may be the 26Fr ARGYLE Nasopharyngeal Airway (Covidien LP, Argyle, NY), which has a length L of about 11 cm, an inner diameter of about 6.5 mm, and outer diameter (W) of about 8.7 mm.

While the inventions have been illustrated and described in detail in the drawings and foregoing description, the same is to be considered as illustrative and not restrictive in character. Only certain embodiments have been shown and described, and all changes, equivalents, and modifications that come within the spirit of the invention described herein are desired to be protected. Any experiments, experimental examples, or experimental results provided herein are intended to be illustrative of the present invention and should not be considered limiting or restrictive with regard to the invention scope. Further, any theory, mechanism of operation, proof, or finding stated herein is meant to further enhance understanding of the present invention and is not intended to limit the present invention in any way to such theory, mechanism of operation, proof, or finding. Thus, the specifics of this description and the attached drawings should not be interpreted to limit the scope of this invention to the specifics thereof.

What is claimed is:

1. A system comprising:
   a main bite block defining upper and lower outer surfaces adapted to be positioned between a patient's upper and lower teeth respectively and defining an operating lumen for providing instrument access;
   wherein the bite block includes an outer face adapted to be positioned outside the patient's mouth during use, the outer face defining a first side opening and a second side opening, wherein the first side opening includes a pair of lips which protrude from the outer face, wherein the first side opening includes a pair of mounting members that extend inwardly from an interior surface of the first side opening in a direction along the longitudinal axis of a nasopharyngeal airway, each of the pair of mounting members has an inwardly tapered engagement surface relative to the longitudinal axis of the nasopharyngeal airway; and
   a nasopharyngeal airway having an outwardly tapered surface relative to the longitudinal axis of the nasopharyngeal airway, the nasopharyngeal airway positioned in the first side opening such that the inwardly tapered engagement surface of each of the pair of mounting members is configured to engage and retain the outwardly tapered surface of the nasopharyngeal airway, the nasopharyngeal airway having a trumpet end configured to engage with the pair of lips in a press fit engagement, the nasopharyngeal airway is adapted to extend distally into the patient's oral cavity to provide an airway for the patient during a medical procedure.

2. The system of claim 1 wherein the nasopharyngeal airway is secured to the bite block.

3. The system of claim 2 wherein the nasopharyngeal airway is secured to the bite block via a mount disposed in the first side opening.

4. The system of claim 3 wherein the mount comprises the pair of mounting members having a plurality of gripping teeth which engage the nasopharyngeal airway.

5. The system of claim 4 wherein the nasopharyngeal airway contacts the interior surface of the first side opening in at least two different locations.

6. The system of claim 5 wherein a substantial portion of the mount is formed integrally with the bite block.

7. The system of claim 1 wherein the bite block includes a side wall thickness, an upper wall thickness, and a lower wall thickness, wherein the side wall thickness is greater than the upper wall thickness and the lower wall thickness.

* * * * *